United States Patent [19]

Bodor et al.

[11] 4,264,765
[45] Apr. 28, 1981

[54] SALTS OF ERYTHROMYCIN A ESTERS

[75] Inventors: Nicholas S. Bodor, Gainesville, Fla.; Leslie A. Freiberg, Waukegan, Ill.

[73] Assignee: Abbott Laboratories, North Chicago, Ill.

[21] Appl. No.: 122,948

[22] Filed: Feb. 20, 1980

[51] Int. Cl.³ .......................................... C07H 17/08
[52] U.S. Cl. .................................. 536/9; 424/180
[58] Field of Search ............................. 536/9

[56] References Cited

U.S. PATENT DOCUMENTS

| 2,857,312 | 10/1958 | Stephens | 536/9 |
| 2,881,163 | 4/1959 | Walasek | 536/9 |
| 3,558,594 | 1/1971 | Jones et al. | 536/9 |

OTHER PUBLICATIONS

Stephens, "Antibiotic Annual", 1953–1954, pp. 514–521.
Noller, "Chem. of Organic Compounds", 3rd Ed., W. B. Saunders Co., 1965, p. 253.

Primary Examiner—Johnnie R. Brown
Attorney, Agent, or Firm—Paul D. Burgauer; Robert L. Niblack

[57] ABSTRACT

Highly water-soluble erythromycin A derivatives wherein the desosamine moiety is quaternized with an acyloxy-, benzoyloxy- or alkoxycarbonyl-(or carboxy)-acylmethyl iodide, bromine or chloride and esterified in the 2-position with loweralkyl or —$(CH_2)_nCO_2R''$, wherein R'' is H, loweralkyl or substituted loweralkyl and n is an integer from 1–5. These new esters readily convert to erythromycin A upon administration to warm-blooded animals.

9 Claims, No Drawings

SALTS OF ERYTHROMYCIN A ESTERS

DETAILED DESCRIPTION OF THE INVENTION

Erythromycin is a widely used antibiotic which has been successfully administered in the form of certain esters or salts to combat numerous infections in warm-blooded animals. Esters and salts have been employed in place of the free erythromycin base to avoid the bitter taste of the base or to alter the solubility of the base in order to produce orally active derivatives which are active in particular sections of the G.I. tract or which have particular absorption characteristics. All of the known esters and salts, however, are either highly basic or water-insoluble and therefore unsuitable for intramuscular injections.

It has now been found that erythromycin A derivatives in which the desosamine moiety has the structure

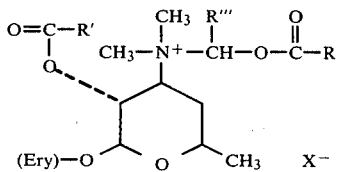

are water-soluble and convert to erythromycin A when administered to a warm-blooded animal, when R is loweralkyl, phenyl or $-(CH_2)_m CO_2 R''$, R' is loweralkyl or $-(CH_2)_n CO_2 R''$, R'' is H or loweralkyl, R''' is H or loweralkyl, X is iodine, bromine or chlorine, m and n independently represent an integer from 1 to 5, and said loweralkyl in R, R' and R'' and said phenyl may be substituted by chlorine, bromine or loweralkoxy groups. For the purpose of this specification, the term "loweralkyl" represents a chain of 1-4 carbon atoms.

The structure I includes a number of potential zwitterion forming compounds, i.e., all those compounds wherein R or R' carry a free carboxylic acid group. These compounds are made from the corresponding analogs in which a benzyloxycarbonyl takes the place of said carboxylic acid group. As will be recognized by the skilled, the mentioned benzyl group can easily be removed to revert to the free carboxylic acid compounds of structure I. The compounds wherein R or R' carries the free carboxy acid group are particularly useful in that they can painlessly be injected into muscle tissue.

The compounds of the present invention have about the same antibacterial spectrum as erythromycin with about the same potency on a molar basis. However, the new compounds are highly water-soluble and are thus well suited for numerous uses not available to the solid esters and salts of erythromycin which are of low water-solubility. The antibacterial spectrum and potency of the new compounds is totally surprising, since the compounds of structure I wherein the 2'-position carries hydroxy are unstable and the usual, simple esters of erythromycin, i.e., the compounds with a customary tertiary amine group, have no intrinsic antibacterial activity.

The compounds of structure I are made by esterifying erythromycin A by well-known methods to the desired 2'-alkanoyl or 2'-alkoxycarbonylalkanoyl erythromycin A, for instance 2'-propionyl- or 2'-ethylsuccinylerythromycin A. Quaternization of the nitrogen function is then carried out with the desired halomethyl ester of formula

wherein R° is an optionally chloro, bromo or loweralkoxy substituted loweralkyl, phenyl, or benzyloxycarbonylloweralkyl and X represents iodine, bromine or chlorine, and R''' is H or loweralkyl. The latter step is preferably carried out in the presence of an inert-solvent and an alkali carbonate or bicarbonate and in an oxygen-free atmosphere. The bromo- and chloromethyl esters of structure II are known materials; their iodo analogs can be made therefrom by known conversion reactions or, the latter can be made in situ in the reaction mixture containing the chloromethyl ester by adding a molar excess of an alkali iodide, i.e., four or more molar equivalents. The conversion of this chloride to the iodide is a rather slow reaction, and thus the quaternization reaction takes many hours, but is much faster than if only the chloromethyl esters were used. In order to prevent discloration, possible degradation of the macrolide moiety and other potential side reactions, the reaction mixture should never be allowed to become acidic, should be kept under a nitrogen atmosphere and at a temperature not exceeding 60° C.

Typical quaternizing agents include iodomethyl pivalates, chloromethyl benzoates, iodomethyl propionates, etc. When the above structure II is an iodoalkyl ester or an alkyl iodide is used to accelerate quaternization, the resulting compound I (X=iodine) can be converted into the chloride salt with NaCl or $CaCl_2$. A highly soluble inert solvent for quaternization is acetonitrile, although proprionitrile, dimethylformamide, dimethylacetamide and the like may be used in its place.

In order to illustrate the preparation of the compounds of structure I, reference is made to the following examples, which, however, are not intended to limit the invention in any respect. In all instances, the rotations given were measured at a concentration of 1.0 in acetonitrile except where stated otherwise, and all compounds showed microanalyses consistent wih the assigned structure.

EXAMPLE 1

A stirred mixture of 3.95 g of 2'-propionyl erythromycin A and 110 ml. of acetonitrile was thoroughly purged with nitrogen. Then 3.01 g of sodium iodide was added and allowed to dissolve followed by 4.2 g of sodium bicarbonate and 0.75 ml. of chloromethyl pivalate (bp 60°-61° C. at 25 torr). The mixture was stirred at 25° C. under a positive nitrogen pressure for three days, was filtered and the solvent was evaporated in vacuo at 40°-45° C. The residue was dried at ambient temperature for 30 minutes at 1-2 torr, followed by the addition of 350 ml. of chloroform and stirring for 45 minutes. The product dissolved, leaving a milky precipitate consisting mainly of sodium iodide. which was removed by filtration through a Celite mat. The chloroform was evaporated at 40°-45° C. and the residue dried at 1-2 torr for 40 minutes. The residue was then stored under 200 ml of benzene for two days, followed by decanting the benzene and drying the product again as before, leaving 4.14 g of crude 2'-propionyl-N-pivalyloxymethylerythromycin A iodide.

A pure sample was obtained by placing this crude material on a column with 50 g of Sephadex LH-20 (a particularly cross-linked dextran gel from Pharmacia, Upsala, Sweden) and eluting with acetonitrile/methonol (19:1) at flow rates of 0.1–0.2 ml/minutes, collecting 1.5 to 3.0 ml fractions. Appropriate fractions were combined and concentrated to dryness after analysis by thin layer chromatograpy on 20 cm plates developed to a height of 30 mm with methanol containing 1% acetic acid, spotted 15 mm from the end and then devloped with EtOH:DMF:HOAc (9:1:0.02) to a height of 135 mm and detected with a cerric sulfate spray reagent followed by heating several minutes to 140° C.

The pure sample is represented by a light yellow powder; ir 1761, 1730 and 1690 cm$^{-1}$; pmr $\delta$ 5.48, 5.28, 5.24, 3.33, 3.22 and 3.08 ppm; $[\alpha]_D^{25} - 60°$.

EXAMPLE 2

By using the procedure of Example 1, but substituting 2'-propionyl erythromycin with 2'-ethylsuccinyl erythormycin and purifying the final product by Sephadex LH-20 chromatography, 2'-ethylsuccinyl-N-pivalyloxymethylerythromycin A iodide was obtained; ir 1758, 1722 and 1685 cm$^{-1}$; pmr $\delta$ 5.40, 5.34, 5.23, 3.33, 3.22 and 3.14 ppm; $[\alpha]_D^{25} - 54°$.

In similar fashion, the compound is prepared wherein the 2'-position carries the propylsuccinyl, butylsuccinyl or the methylsuccinyl group, in each case starting the described reaction with the appropriate erythromycin 2'-alkylsuccinyl ester.

EXAMPLE 3

The quaternary iodide of Example 2 was converted to the corresponding chloride by dissolving 1.78 g of the iodide salt in 100 ml ethyl acetate and 25 ml of methylene chloride, washing the solution with 20 ml of water containing several mg of sodium thiosulfate to remove any yellow color, washing the organic layer repeatedly with 50 ml portions of a saturated sodium chloride solution and evaporating it to dryness at 15°–25° C. In this fashion, 1.27 g of 2'-ethylsuccinyl-N-pivalyloxymethyl erythromycin A chloride was obtained. A purified sample was obtained by the method shown at the end of Example 1. It is a white powder; ir 1758, 1725 and 1685 cm$^{-1}$; pmr 5.53, 5.48, 5.19, 3.34, 3.26 and 3.12 ppm; $[\alpha]_D^{29} - 62°$.

EXAMPLE 4

2'-Propionyl-N-benzoyloxymethyl erythromycin A iodide was prepared from 2'-propionyl erythromycin A and chloromethyl benzoate essentially by the method used in Example 1. A 2.1 g sample of the crude iodide salt was converted to 637 mg of the chloride salt by the method shown in Example 3. A 410 mg sample of this salt was purified by the method shown in Example 1 to produce 165 mg of 2'-propionyl-N-benzoyloxymethyl erythromycin A chloride as a white powder; ir 1747, 1730 and 1690 cm$^{-1}$; pmr 8.10–8.25, 7.45–7.85, 5.83, 5.63, 5.23, 3.33, 3.26 and 3.09 ppm; $[\alpha]_D^{32} - 61°$.

EXAMPLE 5

2'-Ethylsuccinyl erythromycin A (1.0 g.) was reacted with chloromethyl benzoate under the conditions used in Example 1. After 118 hours, the reaction was worked up as described, maintaining all evaporation temperatures below 15° C. Essentially pure 2'-ethylsuccinyl-N-benzoyloxymethyl erythromycin A iodide, 887 mg or 70% of theory, was obtained in essentially pure form; ir 1748, 1725 and 1688 cm$^{-1}$; pmr $\delta$ 8.10–8.25, 7.45–7.85, 5.66, 5.26, 3.34, 3.23 and 3.18 ppm; $[\alpha]_D^{29} - 58°$.

EXAMPLE 6

By the method of Example 1, 3.96 g of 2'-propionyl erythromycin A was reacted with 0.56 ml of chloromethyl propionate, and after 90 hours at room temperature, work-up according to the above method yielded 4.07 g of crude 2'-propionyl-N-propionyloxymethyl erythromycin A iodide.

A 1.78 g sample of this crude iodide salt was converted to 675 mg of the corresponding chloride salt by the method of Example 3. The latter was purified in the described manner to produce 77 mg of 2'-propionyl-N-propionyloxymethyl erythromycin A chloride; ir 1762, 1730 and 1689 cm$^{-1}$; pmr $\delta$ 5.56, 5.31, 5.17, 3.30, 3.18 and 2.99 ppm; $[\alpha]_D^{31} - 65°$.

EXAMPLE 7

2'-Ethylsuccinyl erythromycin A was reacted with chloromethyl propionate in a manner similar to Example 1 except that only 1.5 molar equivalent of sodium iodide was used. Complete reaction was indicated after 240 hrs at 250° C. The residue was purified in the usual fashion, producing a near white powder of 2'-ethylsuccinyl-N-propionyloxymethyl erythromycin A iodide; ir 1765, 1727 and 1690 cm$^{-1}$; pmr $\delta$ 5.35, 5,29, 5.19, 3.32, 3,13 and 3.04 ppm; $[\alpha]_D^{28} - 58°$.

EXAMPLE 8

To a solution of 5 g of succinic acid monobenzyl ester in 60 ml of benzene was added 11 ml of oxalyl chloride. After 5 hrs at 20° C., gas evolution ceased and the solvent and excess oxalyl chloride was evaporated at 20° C. The residue was held at 1 torr for 1 hr to yield 5.19 g of crude benzyl 3-chloroformylpropionate; ir 1788 and 1735 cm$^{-1}$.

To a stirred solution of 16.5 g of erythromycin A in a mixture of 300 ml of acetonitrile and 30 ml of benzene was added 9.5 g of sodium bicarbonate followed by dropwise addition of the above benzyl 3-chloroformylpropionate in 50 ml of benzene over a period of 2 hrs. After standing overnight, insoluble salts were removed by filtration, and the filtrate was concentrated to dryness at 50° C. The residue was placed in 500 ml of chloroform, washed with three 100 ml portions of 1% sodium bicarbonate, dried over sodium sulfate and concentrated to dryness at 50° C. The residue was dried at 450° C. in a vacuum oven to give 18.3 g of crude 2'-benzylsuccinyl erythromycin A. After three crystallizations from aceton/water, 8.7 g of pure material was obtained, melting at 138°–147° C.; ir 1730 and 1682 cm$^{-1}$.

A stirred solution of 1.5 g of the above 2-benzylsuccinyl erythromycin A in 40 ml of acetonitrile was thoroughly purged with nitrogen and 973 mg of sodium iodide was dissolved in the mixture. This was followed by the additional 1.37 g of sodium bicarbonate and 0.275 ml of chloromethyl pivalate. After 70 hrs, the material was worked up as described above to produce 1.02 g of pure 2'-benzylsuccinyl-N-pivalyloxymethyl erythromycin A iodide as a yellow powder; ir 1755, 1725 and 1680 cm$^{-1}$, pmr $\delta$ 7.37, 5.39, 5.34, 5.22, 5.14, 3.32, 3.19 and 3.11 ppm; $[\alpha]_D^{29} - 51°$ C.

EXAMPLE 9

By the procedure shown in Example 3, the product of Example 8 was converted into the corresponding chloride salt; ir 1760, 1730 and 1685 cm$^{-1}$; pmr δ 7.36, 5.35, 5.22, 5.22, 5.14, 3.31, 3.13 and 3.07 ppm; [α]$_D^{29}$ −59°.

EXAMPLE 10

A mixture of 50 ml of methanol and 1.09 g of 5% Pd on carbon was prehydrogenated at 3 atm hydrogen on a Parr shaker for 1 hr. Then 450 mg of the product of Example 9 was added, and after 10 min. on the Parr shaker, the catalyst was removed by suction filtration through Celite. The methanol was immediately evaporated at 5° C. in vacuo, and the residue was dried at 25° C. (1 torr) for 45 min. The sample was dissolved in 6 ml of acetonitrile and a grey precipitate was removed by filtration through Celite. Evaporation of the solvent at 5° C. gave 290 mg of 2′-succinyl-N-pivalyloxymethyl erythromycin A chloride as a white powder; ir 1733 cm$^{-1}$ broad; uv λ$_{max}$ 285$_{nm}$, ε=27; pmr δ 5.45, 5.34, 5.22, 3.32, 3.20 and 3.14 ppm; [α]$_D^{25}$ −62°.

EXAMPLE 11

A sample of 5.03 g of glutaric acid monobenzyl ester was converted to 5.42 g of benzyl 4-chloroformylbutyrate by the method used in Example 8, second paragraph; ir 1974 and 1733 cm$^{-1}$. A crude sample of this material was used to esterify 16.6 g of erythromycin A under the condition shown in Example 8 to yield 7.83 g of 2′-benzylglutaryl erythromycin A after three crystallizations from acetone/water; mp 111°-19° C.; ir 1730 and 1685 cm$^{-1}$; pmr δ 7.37, 5.10, ca. 4.6, 3.31 and 2.16 ppm; [α]$_D^{24}$ −66°.

A stirred solution of 2.5 g of the just described material in 60 ml of acetonitrile at 25° C. was thoroughly purged with nitrogen and 0.6 g of sodium iodide was added, followed by 2.25 g of sodium bicarbonate and 0.44 ml of chloromethylpivalate. After 10 days the reaction mixture was worked up and purified in the above described fashion, producing 3.29 g of 2′-benzylglutaryl-N-pivalyloxymethyl erythromycin A iodide which was converted to the 1.45 g of the corresponding chloride salt in accordance with the above samples. After purification of the latter, it was obtained as a white powder; ir 1762, 1732 and 1690 cm$^{-1}$; pmr δ 7.36, 5.53, 5.37, 5.17, 5.11, 3.30, 3.18 and 3.00 ppm; [α]$_D^{31}$ −55°.

EXAMPLE 12

A sample of 356 mg of the compound of Example 11 dissolved in 50 ml of methanol and 350 mg of 5% Pd on carbon was added under nitrogen. The mixture was hydrogenated at 3 atm for 20 min., followed by the usual work-up in accordance with the above. Purification in the above fashion produced 2′-glutaryl-N-pivalyloxymethyl erythromycin A chloride; mp 141°−7° C.; ir 1734 cm$^{-1}$ broad; uvλ$_{max}$ 285$_{nm}$, ε=29; pmr δ 5.42, 5.30, 5.22, 3.31, 3.15 and 3.09 ppm; [α]$_D$ −56°.

EXAMPLE 13

Pimelic acid monobenzyl ester was prepared according to an adaptation of the method of Hassner et al, Tetrahedron Letters No. 46, 4475 (1970); it boils at 205° C. (1.5 torr). This material was converted to benzyl 6-chloroformylcaproate according to the above methods and 5.25 g of the latter compound was stirred with 0.59 g of paraformaldehyde and several mg of fused zinc chloride and heated to 120° C. in an oil bath. After the paraformaldehyde was consumed (about 1½ hrs), the mixture was cooled, giving 5.73 g of multi-component product. Purification of 3.85 g of this crude product was achieved on a 180 g (2.9×61 cm) column of Silica Gel 60, prepared in a solvent of toluene/chloroform 9:1. The column was run at the flow rate of 1.8 ml/min. and 20 ml fractions were collected. The column was eluted first with 3 liters of toluene/chloroform 9:1, secondly with 3 liters of a 8.5:1.5 mixture of these solvents and finally with 1 liter of toluene containing 15% of chloroform and 7.5% of ethyl acetate. The various fractions were analyzed and combined where appropriate to produce 1.00 g of an oil identified as benzyl chloromethyl pimelate; ir 1765 and 1735 cm$^{-1}$; pmr δ 7.34, 5.68, 5.11, 2.25–2.50 and 1.1–1.9 ppm.

A stirred solution of 1.84 g of 2′-ethylsuccinyl erythromycin A in 40 ml of acetonitrile was thoroughly purged with nitrogen, then 0.46 g of sodium iodide, 1.79 g of sodium bicarbonate and 704 mg of the above pimelate were added. After 12 days at 25° C., the reaction mixture was filtered and the solvent evaporated at 25° C. The residue was rinsed with 10 ml of benzene and then dried at 1 torr for 1 hr to give 2.69 g of crude 2′-ethylsuccinyl-N-[O-benzyl pimelyloxymethyl] erythromycin A iodide.

The crude iodide salt was converted to 2.21 g of the crude chloride analog, and the 490 mg sample was purified using the above methods, producing 367 mg of the desired compound of structure I; ir 1760, 1727 and 1692 cm$^{-1}$; pmr δ 7.36, 5.50, 5.40, 5.17, 5.09, 3.33, 3.20 and 3.04 ppm; [α]$_D^{32}$ −55°.

EXAMPLE 14

A 356 mg sample of the compound of Example 13 was dissolved in 50 ml of methanol and 350 mg of 5% Pd on carbon was added under nitrogen. Hydrogenation, solvent removal and work-up was carried out as described before to produce 2′-ethylsuccinyl-N-pimelyloxymethyl erythromycin chloride in a yield of 405 mg of the pure material; ir 1760, 1725 and 1685 cm$^{-1}$; uvλ$_{max}$ 285 nm, ε=26; pmr δ 5.46, 5.35, 5.17, 3.34, 3.17 and 3.06 ppm; [α]$_D$ −56°.

EXAMPLE 15-24

The compounds listed below are all made in the fashion described in details in preceeding Examples. The following table refers to the appropriate method:

| Example # | R | R′ | R″ | See Ex. 190 |
|---|---|---|---|---|
| 15 | t-Bu | n-C$_3$H$_7$ | n-C$_4$H$_9$* | 1 |
| 16 | o-toluyl | " | H | 4 |
| 17 | p-ClC$_6$H$_4$ | " | H | 4 |
| 18 | m-BrC$_6$H$_4$ | " | H | 4 |
| 19 | p-MeOC$_6$H$_4$ | " | H | 4 |
| 20 | EtOCH$_2$CH$_2$ | " | H | 1 |
| 21 | ClCH$_2$CH$_2$CH$_2$ | " | H | 1 |
| 22 | t-Bu | MeOCH$_2$CH$_2$** | H | 2 |
| 23 | " | 2-BrCH$_2$CH$_2$** | H | 2 |
| 24 | " | 3-Cl(CH$_2$)$_3$** | H | 2 |

*starting material of structure II: -chloropentyl pivalate
**The starting esters are made in the same fashion as 2′-propionylerythromycin A, using active derivatives of methoxy- or bromopropionic acid or chlorobutyric acid for erythromycin A esterification.

EXAMPLE 25

The above compounds were tested per their antibacterial uses in a standard test, using mice infected with Staph, Aureus (Smith). The following table shows the results where the animals had received sufficient inoculation to produce (a) an LD$_{50}$ of 10–100 or (b) an LD$_{50}$ of 100–1000. The compounds of the above examples were administered subcutaneously as isotonic solutions or aqueous solutions buffered to a pH of 7.4.

| Compound of Esters | | LD 50 |
|---|---|---|
| 1 | a | 88 |
| 2 | b | 143 |
| 3 | a | 58 |
| 4 | b | 40 |
| 5 | 100 | 52 |
| 7 | 100 | 24 |
| 10 | a | 37 |
| 12 | b | 73 |
| 14 | a | 47 |

The new quaternary ammonium salts of erythromycin esters of the present invention are made by reacting the appropriate erythromycin 2'-ester with the compound of formula II wherein R° and R''' have the above defined meanings and X stands for iodine or chlorine in an aprotic, polar reaction solvent at a temperature below 30° C. for a period of at least 24 hrs. At room temperature, the reaction is preferably continued for 48-72 hrs or longer, although substantial quaternization takes place in the first 24 hrs. Periods of more than 72 hrs usually do not produce an increase in yield sufficient to justify the additional time spent. When II is a chloromethyl ester, the reaction is preferably carried out in the presence of a molar excess of an alkali iodide, preferably sodium or potassium iodide. While the reaction between an erythromycin R'-ester (R' is loweralkyl, carboxyloweralkyl or carbalkoxyalkyl) and II proceeds under the above given conditions, the reaction is preferably carried out in an oxygen-free atmosphere and in the presence of an alkali carbonate or bicarbonate to minimize formation of by-products or degradation products. Preferred alkali carbonates or bicarbonates include potassium carbonate, sodium bicarbonate and the like.

The new compounds of formula I have antibacterial activities corresponding to those of the free erythromycin base with the same potency based on equal molecular ratios. Thus, the new salts can be administered in the same fashion and for the same purpose to warm-blooded animals in the customary solid dosage forms, such as pills, tablets, wafers, powders or capsules. In addition, the new salts are highly water-soluble and therefore they can easily be incorporated into liquid dosage forms, such as syrups, elixirs or the like, or they may be supplied in cachets for the in situ preparation of an aqueous dosage form. This use is particularly advantageous for pediatric and geriatric uses. Also, the new compounds are well suited for intravenous injections or infusions where such therapy is needed. Neutral liquid dosage forms are far more stable than the customary erythromycin esters or salts thereof: they have a half-life of 5-50 hrs while older forms show a half-life of 30-60 min.

I claim:

1. A quaternary erythromycin salt of erythromycin A 2'-ester wherein the desosamine moiety has a partial structure of the formula

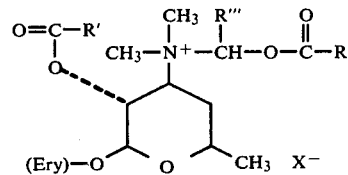

wherein (Ery) represents erythromycin A, R is loweralkyl, phenyl or —(CH$_2$)$_m$COOR", R' is loweralkyl, or —(CH$_2$)$_n$COOR", R" is H or loweralkyl, X is bromine, iodine or chlorine, R''' is H or loweralkyl, m and n independently represent an integer from 1 to 5, and said loweralkyl in R, R' and R" and said phenyl may be substituted by Cl, Br or loweralkoxy.

2. A salt as defined in claim 1 wherein R is tert. butyl.

3. The salt of claim 2 wherein R' is ethoxycarbonylethyl and R''' is H.

4. The salt of claim 2 wherein R' is carboxyloweralkyl and R''' is H.

5. The salt of claim 4 wherein said loweralkyl is propyl.

6. The salt of claim 1 wherein R is phenyl and R''' is H.

7. The salt of claim 6 wherein R' is ethoxycarbonylethyl.

8. The salt of claim 6 wherein R' is ethyl and R''' is H.

9. A salt as defined in claim 1 wherein R is loweralkyl and R' is ethyl or ethoxycarbonylethyl.

* * * * *